US005639629A

United States Patent [19]
Repine et al.

[11] Patent Number: 5,639,629
[45] Date of Patent: Jun. 17, 1997

[54] METHOD OF USING LDH AS A PREDICTOR OF THE ADULT RESPIRATORY DISTRESS SYNDROME IN SEPTIC PATIENTS

[75] Inventors: John E. Repine, Englewood; Jonathan A. Leff, Littleton, both of Colo.

[73] Assignees: The Regents of the University of Colorado, Boulder; The Webb-Waring Institute for Biomedical Research, Denver, both of Colo.

[21] Appl. No.: 347,290

[22] Filed: Nov. 30, 1994

Related U.S. Application Data

[62] Division of Ser. No. 34,935, Mar. 19, 1993, Pat. No. 5,389,522.

[51] Int. Cl.⁶ .................... C12Q 1/32; C12Q 1/30
[52] U.S. Cl. .................... 435/26; 435/13; 435/27
[58] Field of Search .................... 435/26, 7.4, 13, 435/27; 436/811

[56] References Cited

U.S. PATENT DOCUMENTS 5,389,522  2/1995  Repine .................... 435/7.4

OTHER PUBLICATIONS

Ward, P., Systemic Complement Activation, Lung Injury... J Clin Invest 76 Aug. 1985 517–527.
Dwenger, A., Nonspecific Immune System... Adult Respiration Distress Syndrome, Springer Verlag, Berlin, 1991 pp. 91–127.
Montaner J., Multisystem Organ Failure Predicts... Chest 102 (6) Dec 1992 pp. 1823–1828 (C42).
Leff J., Serum Antioxidants As Predictors Of Adult... Lancet 341 Mar. 27, 1993 pp. 777–780.
Wang Y., Protective Effect Of Heat Shock Response On Oleic Acid Induced Lung Injury In Rats, Hunan Yike Daxue Xuebao 17(4) 1992 pp. 337–339.

*Primary Examiner*—Ralph Gitomer
*Attorney, Agent, or Firm*—Marshall, O'Toole, Gerstein, Murray & Borun

[57] ABSTRACT

At the initial diagnosis of sepsis (6–24 h before the development of ARDS), serum lactate dehydrogenase (LDH) activity level is increased in septic patients who subsequently develop ARDS compared to healthy patients and septic patients who do not develop ARDS. A method is disclosed for predicting the occurrence of ARDS in a septic patient from the patient's serum level of LDH activity, which method facilitates identification of subsets of patients destined to develop ARDS and allows prospective treatment of such septic patients.

14 Claims, 2 Drawing Sheets

METHOD OF USING LDH AS A PREDICTOR OF THE ADULT RESPIRATORY DISTRESS SYNDROME IN SEPTIC PATIENTS

This invention was made with Government support under contracts HL 01849, HL 40784, and HL 45582 awarded by the National Institutes of Health. The Government has certain rights in this invention.

This application is a divisional of U.S. patent application Ser. No. 08/034,935, filed Mar. 19, 1993, now U.S. Pat. No. 5,389,522.

BACKGROUND

The present application relates in general to methods and apparatus for performing assays for disease states, and in particular to methods and apparatus for performing assays for adult respiratory distressed syndrome (ARDS).

ARDS is an acute inflammatory process characterized by lung neutrophil accumulation, lung edema and progressive hypoxemia [Repine, *Lancet*, 339, 466–469 (1992)]. ARDS occurs as a complicating factor in patients with sepsis as well as numerous other predisposing conditions. Since many common and diverse risk factors lead to the development of ARDS, but ARDS develops only relatively rarely, pretreating everyone at risk for ARDS is not practical [Fowler et al., *Ann. Intern. Med.*, 98, 593–597 (1983)]. Because a better understanding of ARDS is emerging and various interventions which can limit inflammation are forthcoming, it has become a major goal to identify accessible and repeatable markers in at risk patients which predict the development of ARDS. This will enable experimental therapies to be prospectively and effectively evaluated in smaller, better-defined groups of patients.

SUMMARY OF THE INVENTION

The present invention provides a method for identifying septic patients for prospective treatment of adult respiratory distress syndrome including the step of determining a high (greater than an established baseline) serum level of manganese superoxide dismutase.

The present invention also provides a method for identifying septic patients for prospective treatment of adult respiratory distress syndrome including the step of determining a high (greater than an established baseline) serum level of catalase.

According to the present invention, apparatus for identifying septic patients for prospective treatment of adult respiratory distress syndrome includes means for determining a high (greater than an established baseline) serum level of manganese superoxide dismutase.

The present invention also provides apparatus for identifying septic patients for prospective treatment of adult respiratory distress syndrome including means for determining a high (greater than an established baseline) serum level of catalase.

Figure 1:
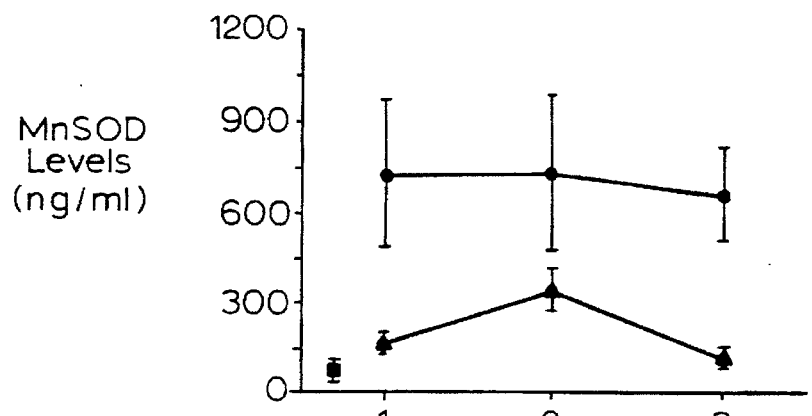
FIG. 1 is a graph of MnSOD levels for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)

In the experiments illustrated in FIGS. 1–6, septic patients were enrolled (0 h) and studied sequentially for the next 48 h. Points were plotted at the diagnosis of sepsis (0 h at 1), at the diagnosis of ARDS (6–24 h after the diagnosis of sepsis at 2) and after the diagnosis of sepsis (6–24 h after the diagnosis of ARDS at 3). Each value is the mean ±SE of 3–20 determinations.

DETAILED DESCRIPTION OF THE INVENTION

In the present investigation, three antioxidant enzymes [manganese superoxide dismutase (MnSOD), catalase and glutathione peroxidase (GPX)] were compared with three other potential markers [Factor VIII [Carvalho et al., *N. Engl. J. Med.*, 307, 1113–1119 (1982) and Rubin et al., *J. Clin. Invest.*, 86, 474–480 (1990)] LDH [Ward et al., *J. Clin. Invest.* 76, 517–527 (1985) and Dwenger et al., In: Sturm, ed. *Adult Respiratory Distress Syndrome*, Berlin Heidelberg: Springer-Verlag, 91–127 (1991)]] and $\alpha_1$Pi-elastase complexes [Rocker et al., *Lancet*, 1, 120–123 (1989) and Hilgenfeldt et al., *Eur. J. Clin. Pharmacol*, 38, 125–131 (1990)] for their ability to predict the development of ARDS in patients with sepsis.

Alterations occur in the oxidant-antioxidant balance in ARDS and in other disease states that appear to involve oxygen radicals in their pathogenesis [Leff et al., *Free Radical Biol. Med.*, 13, 143–149 (1992); Leff et al., *Am. Rev. Respir. Dis*, 146, 985–989 (1992); Buhl et al., *Lancet*, 2, 1294–1298 (1989); Bernard et al., *Am. Rev. Resp. Dis.*, 139, A221 (Abstract) (1989); and Pacht et al., *Chest*, 100, 1397–1403 (1991)]. In addition, patients with established ARDS have elevated serum catalase activity [Leff et al., *Am. Rev. Respir. Dis*, 146, 985–989 (1992)]. Serum catalase activity increased in a rat model of burn-induced acute lung injury [Leff et al., *Inflammation* (In Press) (1992)].

EXAMPLE

Patient Consent and Selection. After written consent was obtained from the patient or a family member, each subject was studied using a protocol which was approved by an institutional human subjects review committee. All patients (n=26) who were identified within 8 h of the diagnosis of sepsis were eligible for enrollment. Patients with sepsis had a serious bacterial infection and either (a) a rectal or core temperature exceeding 39° C. or (b) a peripheral leukocyte count of >12,000 cells/mm$^3$ or >20% immature neutrophils. Septic patients also had at least one of the following: a positive blood culture involving a commonly accepted pathogen, a strongly suspected or proven source of systemic infection, gross pus in a closed space, unexplained systemic arterial hypotension (systolic blood pressure less than 80 mm Hg), systemic vascular resistance less than 800 dyn× s×cm$^2$ and/or unexplained metabolic acidosis [Parsons et al., Am. Rev. Resp. Dis., 140, 294–301 (1989)].

Patients with ARDS (n=6) met the following criteria: (1) acute respiratory failure requiring mechanical ventilation, (2) bilateral pulmonary infiltrates, (3) pulmonary capillary wedge pressure <18 mm Hg, (4) static pulmonary compliance <50 ml/cm H$_2$O, and (5) arterial to alveolar partial pressure of oxygen ratio of <0.25 [Parsons et al., Am. Rev. Resp. Dis., 140, 294–301 (1989)]. Serum and plasma samples were obtained at the diagnosis of sepsis (0 h) and at the diagnosis of ARDS (6–24 h after the diagnosis of sepsis) and after the diagnosis of ARDS (6–24 h after the diagnosis of ARDS) either through an indwelling arterial or venous catheter or by direct venipuncture. Patients were divided into two groups: septic patients who did not develop ARDS and septic patients who later developed ARDS. Patients were prospectively and sequentially studied until death or discharge. All assays were performed by personnel who were unaware of the diagnoses. Control subjects (n=15) were healthy individuals.

Source of reagents. Hanks' balanced salt solution (HBSS) was purchased from Gibco Laboratories (Grand Island, N.Y.). All other reagents were obtained from Sigma Chemical Company (St. Louis, Mo.).

Measurement of serum markers. MnSOD [Kawaguchi et al., Biochem. Biophys. Res. Commun. 171, 1378–1386 (1990)], Factor VIII antigen [Cejka, Clin. Chem., 28(6), 1356–1358 (1982)] and $\alpha_1$Pi-elastase complexes [Duswald et al., Surgery, 98, 892–899 (1985)] were measured by ELISA. Catalase was assessed by polarographic assessment of O$_2$ evolution [Leff et al., J. Appl. Physiol., 71(5), 1903–1906 (1991)]. GPX was measured as the oxidation of NADPH at 340 nm in glutathione reductase, glutathione and t-butyl hydroperoxide [Beutler, A Manual of Biochemical Methods, Orlando, Grune & Stratton, Inc., 1–172 (1984)], LDH [Beutler, A Manual of Biochemical Methods, Orlando, Grune & Stratton, Inc., 1–172 (1984)] and albumin [Corcoran et al., Clin. Chem., 23, 765–766 (1977)] were assayed spectrophotometrically. Uric acid was measured by HPLC [Terada et al., J. Appl. Physiol., 65, 2349–2353 (1988)].

Statistical analyses. Patient groups were compared using an analysis of variance with a Student-Newman-Keuls test of multiple comparisons. An unpaired t test was used to compare the clinical characteristics of septic patients with or without ARDS. For calculations of sensitivity, specificity, positive or negative predictive values and efficiency, 95% confidence intervals were determined based on the binomial distribution [Cochran, In: Sampling Techniques, 2nd ed., New York, John Wiley & Sons, Inc., 54–59 (1963)]. Significance was accepted at a p value of <0.05.

Clinical Parameters. Septic patients who subsequently developed ARDS and septic patients who did not develop ARDS were the same (p>0.05) with respect to age, gender, hematocrit, hemoglobin, blood leukocyte count, blood neutrophil count, serum SGOT, bilirubin, albumin, uric acid levels and APACHE II score [Leff et al., Ann. Rev. Respir. Dis., 146, 985–989 (1992); Knaus et al., Crit. Care Med., 13, 818–289 (1985)]. The mortality of septic patients who developed ARDS was 50% (3 of 6) compared to a mortality of 30% (6 of 20) in septic patients who did not develop ARDS.

Blood markers patterns. Septic patients had increased (p<0.05) serum MnSOD levels compared to control subjects (FIG. 1). However, at the initial diagnosis of sepsis (approximately 6–24 h before diagnosis of ARDS), septic patients who eventually developed ARDS had increased (p<0.05) serum MnSOD levels compared to septic patients who did not develop ARDS. Serum MnSOD levels remained elevated for the next 48 h in patients who developed ARDS while MnSOD levels returned to control levels during the next 48 h in septic patients who did not develop ARDS.

Figure 2:
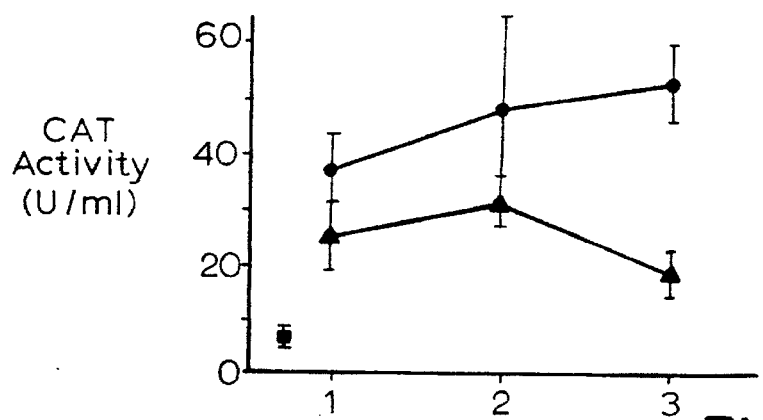
FIG. 2 is a graph of CAT activity for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)

Similarly, at the diagnosis of sepsis, serum from septic patients had more (p<0.05) catalase activity than serum from control subjects. Again, at the initial diagnosis of sepsis, patients who later developed ARDS had more (p<0.05) serum catalase activity than septic patients who did not develop ARDS (FIG. 2). During the next 48 h, serum catalase activity increased progressively in septic patients who developed ARDS but did not change in septic patients who did not develop ARDS.

Figure 3:
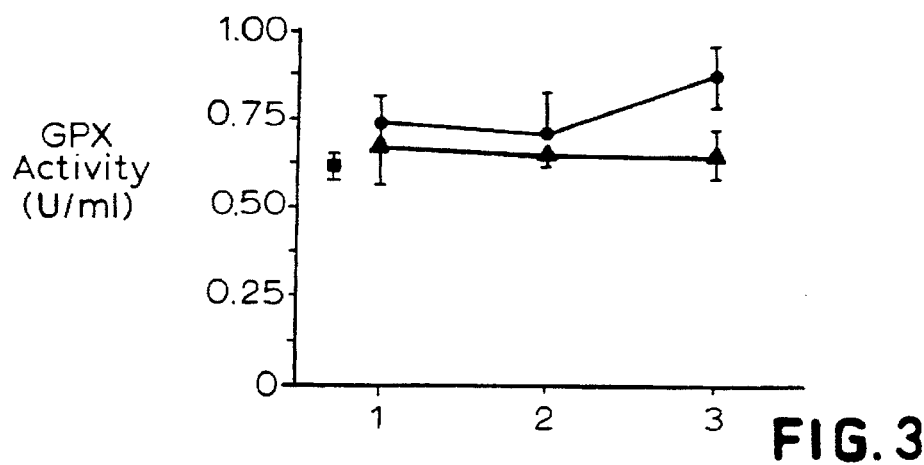
FIG. 3 is a graph of GPX activity for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)

In contrast to MnSOD levels and catalase activities, serum GPX activity was essentially the same (p>0.05) in control subjects and septic patients regardless of whether ARDS ensued (FIG. 3).

Figure 4:
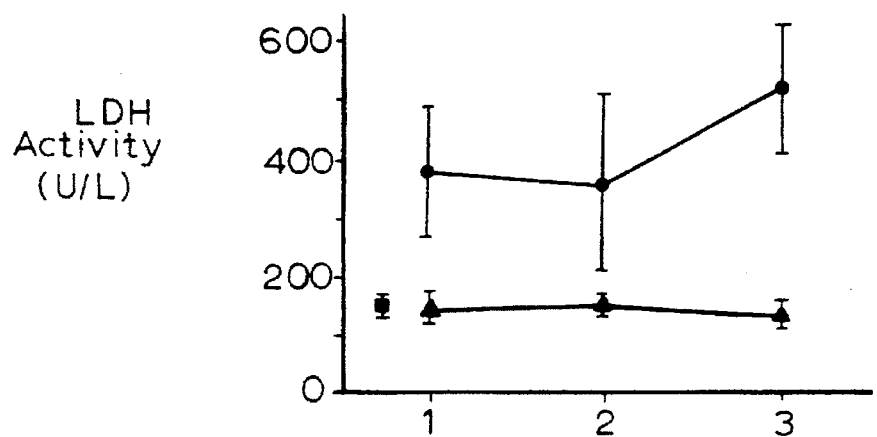
FIG. 4 is a graph of LDH activity for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)
Figure 5:
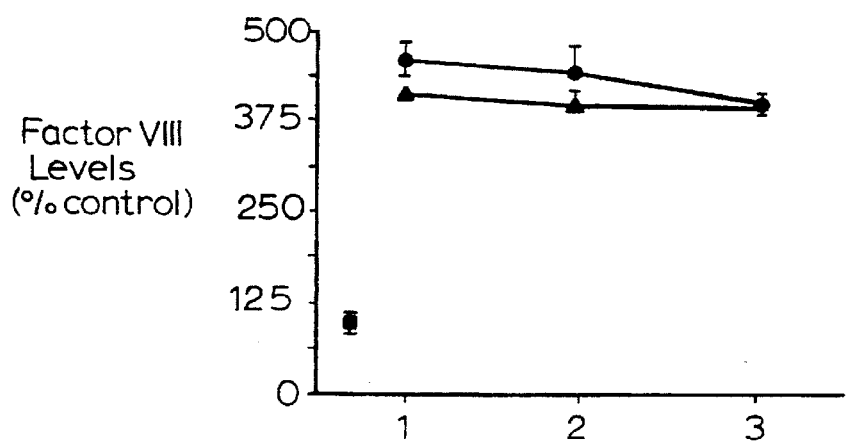
FIG. 5 is a graph of Factor VIII levels for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3)

Serum from septic patients who subsequently developed ARDS also had increased (p<0.05) LDH activity compared to serum from septic patients who did not develop ARDS. Serum from septic patients who did not develop ARDS had the same (p>0.05) LDH activity as serum from control subjects (FIG. 4). Serum LDH measurements increased during the 48 h study period in septic patients who developed ARDS but not in septic patients who did not develop ARDS.

Septic patients who did or did not develop ARDS (FIG. 5) had similarly increased (p<0.05) serum Factor VIII levels compared to control subjects. Septic patients who did and did not develop ARDS had similar (p>0.05) Factor VIII levels.

Figure 6:
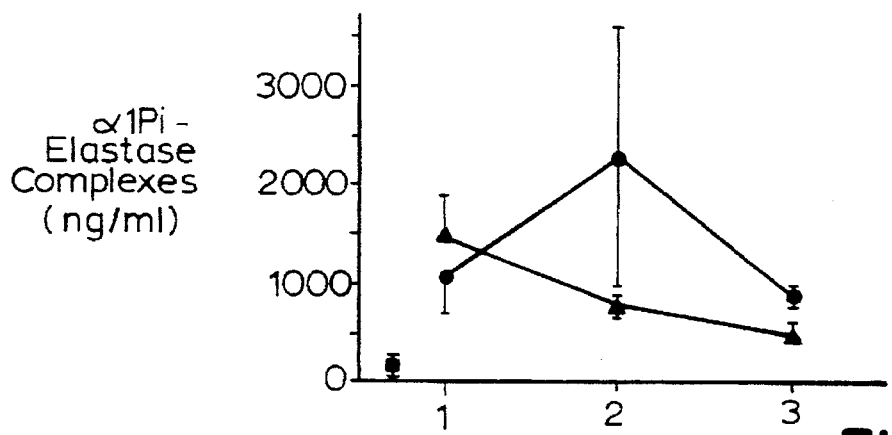
FIG. 6 is a graph of levels of $\alpha_1$Pi-elastase complexes for healthy control subjects (squares); and of septic patients who did not develop ARDS (triangles) and septic patients who developed ARDS (circles) at three times: at diagnosis of sepsis (1), at diagnosis of ARDS (2) and after diagnosis of ARDS (3).

Finally, plasma $\alpha_1$Pi-elastase complexes were increased in all septic patients at the initial diagnosis of sepsis but differences between septic patients who did or did not develop ARDS were manifest only at the time of diagnosis of ARDS (6–24 h after the diagnosis of sepsis) (FIG. 6). By 48 h after the initial diagnosis of sepsis, $\alpha_1$Pi-elastase complexes had similarly decreased in septic patients independent of the development of ARDS.

Analyses of serum markers. First, no correlations were found at any time between any of the six markers; Second, the positive and negative predictive values and the sensitivity and specificity of Serum MnSOD levels (±450 ng/ml), catalase activity (±30 U/ml), LDH activity ±250 U/L and Factor VIII levels ±445% control were comparable in predicting the development of ARDS in septic patients (Table 1). Third, serum MnSOD levels, catalase and LDH activity exceeded 450 ng/ml, 30 U/ml and 250 U/L, respectively, approximately 9 h, 12 h and 12 h, on average, respectively, before the diagnosis of ARDS. Further results appear in Table 1.

TABLE 1

Comparison of the Sensitivity and Specificity of Blood Markers as Predictors of ARDS in Septic Patients

| Parameter | Sensitivity | Specificity | Positive Predictive Value | Negative Predictive Value | Efficiency |
|---|---|---|---|---|---|
| MnSOD ≥ 450 ng/ml | 67% (42-94) | 88% (75-98) | 67% (4-94) | 88% (75-98) | 83% (70-94) |
| Catalase ≥ 30 U/ml | 83% (61-99) | 65% (49-82) | 42% (25-68) | 93% (81-100) | 69% (55-84) |
| GPX ≥ 0.72 U/ml | 50% (27-85) | 47% (31-69) | 25% (12-53) | 73% (53-92) | 48% (34-66) |
| LDH ≥ 250 U/L | 67% (42-94) | 78% (62-92) | 50% (29-81) | 88% (74-98) | 75% (61-89) |
| Factor VIII ≥ 445% Control | 83% (61-99) | 67% (42-94) | 45% (27-73) | 92% (80-100) | 71% (57-85) |
| $\alpha_1$Pi-elastase > 940 ng/ml | 67% (37-98) | 64% (50-80) | 18% (8-47) | 94% (84-100) | 64% (51-79) |

In Table 1 each value represents 3-20 determinations at study entry (t=0 h). Values in parentheses represent 95% confidence intervals. Also in Table 1; Sensitivity=TP/TP+FN; Specificity=TN/TN+FP; Positive Predictive Value=TP/TP+FP; Negative Predictive Value=TN/TN+FN; and Efficiency=TP+TN/TP+FP+TN+FN.

In Table 1, results are shown for six sequentially measured factors in the blood of septic patients who were predisposed to develop ARDS. Nine to twelve hours before the development of ARDS, two serum antioxidant enzymes, MnSOD and catalase, were increased in septic patients who later developed ARDS compared to septic patients who did not develop ARDS and that both of these factors predicted the development of ARDS in septic patients with as good a sensitivity, specificity and efficiency as measurements of LDH and Factor VIII. By comparison, measurements of GPX and $\alpha_1$Pi-elastase complexes were neither different in septic patients who did or did not subsequently develop ARDS nor effective in predicting the development of ARDS in septic patients.

Assessment of MnSOD and catalase are useful for defining the pathogenesis of ARDS or identifying patients with similar pathophysiologies. Each measurement is accessible, repeatable and relatively easy to perform. Based on assessment of these markers, study of prophylactic treatment is facilitated by reducing the number of at risk individuals who need to be studied to obtain patients with ARDS.

Increases in serum MnSOD levels and serum catalase activity may also have functional importance. MnSOD and catalase may diminish oxidant insults mediated by superoxide anion($O_{-2}$.) or hydrogen peroxide ($H_2O_2$) or their products such as hydroxyl radical (.OH). This possibility may be especially relevant because accelerated intravascular generation of oxygen radicals from stimulated neutrophils, circulating xanthine oxidase or other sources are implicated in the pathogenesis of sepsis and ARDS [McGuire et al., J. Clin. Invest., 69, 543-553 (1982); Cochrane et al., J. Clin. Invest. 71, 754-758; (1983); Baldwin et al., Lancet, 1, 11-14 (1986) and Grum et al., J. Crit. Care, 2, 22-26 (1987)].

Because the patterns were different for various markers and no two markers correlated with each other, each factor may represent a distinct process and these factors may more correctly reflect various processes occurring in septic patients with ARDS rather than ARDS per se. The present work has focused on sepsis-induced ARDS, so different mechanisms may be present in patients who develop ARDS following trauma and other predispositions.

The origins of the factors, although unclear, most likely are multiple. Lung tissue injury is a possible source for increases in LDH, MnSOD, catalase and Factor VIII levels. Endothelial cells are rich in these factors and, if perturbed, may readily increase the levels of these factors in the blood. However, intravascular neutrophil activation may be responsible for increases in $\alpha_1$Pi-elastase complexes because elastase may be present only in neutrophils. Notably, increases in $\alpha_1$Pi-elastase complexes occurred relatively later, at the diagnosis of ARDS, and then decreased by 48 h after the diagnosis of sepsis, which may indicate a decline in neutrophil activity. Red blood cell (RBC) hemolysis may be a source for increases in serum catalase and LDH activity, but not MnSOD or Factor VIII levels may not, because RBCs do not contain the latter. Serum catalase activity is also increased in the serum of rats subjected to skin burn [Leff et al., Inflammation (In Press) (1992)], and patients with the acquired immunodeficiency syndrome [Leff et al., Am. Rev. Respir. Dis, 146, 985-989 (1992)], but again, in these situations, the source is unclear. Elevations of IL-1, tumor necrosis factor (TNF) and endotoxin have been found in ARDS patients [Parsons et al., Am. Rev. Resp. Dis., 140, 294-301 (1989); Suter et al., Am. Rev. Resp. Dis., 145, 1016-1022 (1992); Siler et al., Exp. Lung Res., 15(6), 881-894 (1989); Hyers et al., Am. Rev. Respir. Dis., 144, 268-271 (1991) and Marks et al., Am. Rev. Resp. Dis., 141, 94-97 (1990)] and may cause increases in antioxidants such as MnSOD and catalase [White et al., J. Appl. Physiol., 66, 1003-1007 (1989); Wong et al., Science, 242, 941-944 (1988); Brown et al., Proc. Natl. Acad. Sci. (USA), 86, 2516-2520 (1989) and Taniguchi, Adv. Clin. Chem., 29, 1-59 (1992)].

Although the present invention is illustrated by the above embodiments, it is expected that variations and modifications will occur to those skilled in the art upon consideration of the present disclosure. Accordingly, it is intended that the present invention include all modifications and variations which come within the scope of the claims.

What is claimed is:

1. A method for predicting the development of adult respiratory distress syndrome (ARDS) in a septic patient comprising the steps of providing serum of a septic patient, determining said septic patient's serum level of lactate dehydrogenase (LDH) activity, comparing said septic patient's serum level of LDH activity to an established baseline serum level of LDH activity, wherein a serum level of LDH activity greater than said established baseline serum level of LDH activity is predictive of the development of ARDS in septic patients, and predicting the development of ARDS in said septic patient if said septic patient's serum level of LDH activity is greater than said established baseline serum level of LDH activity.

2. The method of claim 1 wherein the esablished baseline serum level of LDH activity is 250 U/L.

3. A method for assessing a septic patient's risk for developing adult respiratory distress syndrome (ARDS) comprising the steps of determining a septic patient's serum level of lactate dehydrogenase (LDH) activity, determining a difference between said septic patient's serum level of LDH activity and a serum level of LDH activity of healthy human subjects, and assessing said septic patient's risk for developing ARDS from said difference, wherein a septic patient with a serum level of LDH significantly greater than a serum level of LDH activity of healthy human subjects has an increased risk for developing ARDS.

4. A method for predicting the development of adult respiratory distress syndrome (ARDS) in a septic patient comprising the steps of determining a septic patient's serum level of lactate dehydrogenase (LDH) activity, and predicting the development of ARDS in said septic patient if said septic patient's serum level of LDH activity is greater than or equal to 250 U/L.

5. A method for predicting the development of adult respiratory distress syndrome (ARDS) in a septic patient, comprising the steps of: determining a septic patient's serum level of lactate dehydrogenase (LDH) activity, performing a comparison of said septic patient's serum level of LDH activity to a baseline serum level of LDH activity, and predicting the development of ARDS in said septic patient from said comparison, wherein a serum level of LDH activity greater than said baseline serum level of LDH activity is predictive of the development of ARDS in septic patients.

6. A method for determining a probability of a septic patient developing adult respiratory distress syndrome (ARDS) comprising the steps of determining a septic patient's serum level of lactate dehydrogenase (LDH) activity, determining a difference between said septic patient's serum level of LDH activity and a serum level of LDH activity of healthy human subjects, and determining a probability of the septic patient developing ARDS from said difference, wherein a serum level of LDH in a septic patient that is significantly greater than a serum level of LDH activity of healthy human subjects is correlated with an increased probability of said septic patient developing ARDS.

7. A method for predicting the development of adult respiratory distress syndrome (ARDS) in a septic patient comprising the steps of:

(a) determining patient's serum level of lactate dehydrogenase (LDH) activity;

(b) determining said patient's serum level of at least one additional ARDS marker selected from the group consisting of manganese superoxide dismutase (MnSOD), catalase activity, and Factor VIII;

(c) performing a comparison of said septic patient's serum level of LDH activity to a baseline serum level of LDH activity, wherein a serum level of LDH activity greater than said baseline serum level of LDH activity is predictive of the development of ARDS in septic patients;

(d) performing a comparison of said septic patient's serum level of said at least one additional ARDS marker to a baseline serum level of said at least one additional ARDS marker, wherein a serum level of said at least one additional ARDS marker greater than said baseline serum level of said at least one additional ARDS marker is predictive of the development of ARDS in septic patients; and (e) predicting the development of ARDS in said septic patient from said comparisons.

8. The method of claim 7 wherein said at least on additional ARDS maker is MnSOD.

9. The method of claim 7 wherein said at least one additional ARDS maker is catalase activity.

10. The method of claim 7 wherein said at least one additional ARDS marker is Factor VIII.

11. The method of claim 7 wherein said least one additional ARDS maker is MnSOD and catalase activity.

12. The method of claim 7 wherein said at least one additional ARDS maker is MnSOD and Factor VIII.

13. The method of claim 7 wherein said at least one additional ARDS maker MnSOD, catalase activity, and Factor VIII.

14. The method of claim 7 wherein said at least one additional ARDS maker is catalase activity and Factor VIII.

* * * * *